United States Patent [19]

Mochida et al.

[11] Patent Number: 5,642,996
[45] Date of Patent: Jul. 1, 1997

[54] ENDOSSEOUS IMPLANT

[75] Inventors: Masaaki Mochida, Yamato; Norio Kaneko, Yokohama; Nobuhiro Tanaka, Zama, all of Japan

[73] Assignee: Nikon Corporation, Tokyo, Japan

[21] Appl. No.: 673,096

[22] Filed: Jul. 1, 1996

Related U.S. Application Data

[63] Continuation of Ser. No. 325,618, Oct. 19, 1994, abandoned.

[30] Foreign Application Priority Data

| Oct. 20, 1993 | [JP] | Japan | 5-261437 |
| Apr. 6, 1994 | [JP] | Japan | 6-068224 |
| Apr. 7, 1994 | [JP] | Japan | 6-069211 |

[51] Int. Cl.$^6$ .................................................. A61C 8/00
[52] U.S. Cl. ............................................................ 433/174
[58] Field of Search .................................. 433/173, 174, 433/175, 176

[56] References Cited

U.S. PATENT DOCUMENTS

| 5,064,425 | 11/1991 | Brånemark et al. | 606/72 |
| 5,205,745 | 4/1993 | Kamiya et al. | 433/173 |
| 5,269,685 | 12/1993 | Jörnéus et al. | 433/174 |
| 5,338,197 | 8/1994 | Kwan | 433/174 |

FOREIGN PATENT DOCUMENTS

| 50-21015 | 3/1975 | Japan. |
| 51-106114 | 9/1976 | Japan. |
| 53-145394 | 12/1978 | Japan. |
| 54-17 | 1/1979 | Japan. |
| 54-135496 | 10/1979 | Japan. |
| 57-3739 | 1/1982 | Japan. |
| 58-118746 | 7/1983 | Japan. |
| 62-52163 | 3/1987 | Japan. |

OTHER PUBLICATIONS

Hench, L.L., Splinter, R.J., Allen, W.C., and Greenlee, T.K. Bonding Mechanisms at the Interface of Ceramic Prostetic Materials, 1971, oo, 117–141, No. 2 (part 1).

Primary Examiner—Christopher A. Bennett

[57] ABSTRACT

A cylinder-type endosseous implant having a collar portion and a main type body portion formed under the collar portion. The implant also has screw threads, wherein the height of said screw threads is 0.2 to 0.4 mm; the pitch of said screw threads is 0.8 to 1.7 mm and the rising angle of said screw threads is determined to be at least 50° and less than 90°. The rising angle is defined to be the angle made by a root surface of the main body portion and the straight line which could be drawn from the top of a screw thread to the bottom of the same screw thread.

19 Claims, 3 Drawing Sheets

ENDOSSEOUS IMPLANT

This application is a continuation of application Ser. No. 08/325,618, filed Oct. 19, 1994, now abandoned.

BACKGROUND OF THE INVENTION

1. Field of the Invention

The present invention relates to improvements for an endosseous implant which is applied to dental use and maxillofacial prosthetics.

2. Related Background Art

Endosseous implants (hereinafter referred as simply "implants") currently available for dental use are classified into two types: those of blade type and those of cylinder type.

A blade-type implant which is formed in the shape of a blade or a plate is used to repair tooth deficiency of a in any part in the jaw bone, but especially to repair free end deficiency of a dens premolaris or a dens molaris. Inside the bone surface, beneath dentes premolaris and dentes molaris, there are inferior alveolar canals. As a result, long implants can not be buried therein and wide blade-type implants are usually used. A perforated site (a prepared hole for implantation) is formed with a drill whose diameter coincides with the width of the blade-type implant employed. As the perforated site is formed by moving the drill in the mesiodistal directions, the shape of the perforation may often be deformed.

A cylinder-type implant which is formed in the shape of a column can also be buried of any part in the jaw bone. The perforated site for this cylinder type implant is formed as a cylindrical hole having more exact dimensions corresponding to the diameter of the implant than the perforated site for the blade-type implant. The diameter of a cylinder-type implant (including thread ridges) is limited from about 3 to 5 mm depending on the width of the jaw bone.

The method of operation employed for implantation of the blade-type implant is the push-in method, while either push-in method or thread-fastening method can be employed for implantation of the cylinder-type implant.

Generally speaking, there are two types of implants with respect to fixation to the bone surface. That is, some implants are fixed to the bone surface, several months after implantation, with fibrous tissue intervening between the implants and the bone, while the other type of implants are made of materials which are directly attached and/or bonded to the bone. The latter has been in the main current because stability can be secured over a long period of time.

The surfaces of an implant which comes in direct contact with the bone when buried may be mechanically worked and be surfaced relatively smoothly. Or the implant may be subjected to physical treatment (typical examples include sand blasting finish, plasma spray, and so on) and/or chemical treatment (such as etching with an acid, anodic oxidation, and so on) to have rough surfaces, which improves affinity with the bone.

When such rough surfaces of the implant are buried in and come into contact with the bone, however, food and various germs in the oral cavity may sometimes enter the interface between the implant and the bone, and the gingiva in the vicinity of the dental neck (the upper portion of the main body beneath the collar) may infected with such germs and suffer from inflammation. In this case, bone resorption further advances, and sometimes the implant comes out. On the other hand, when the implant is smoothly surfaced, food and various germs in the oral cavity which enter the interface between the implant and the bone can be easily removed with a tooth brush. Thus, prevention of infection with germs and inflammation caused by such germs is easy.

Accordingly, only the main body of a typical implant of direct contact type has rough surfaces, while the collar thereof has smooth surfaces.

An implant consists of two parts. The upper part smoothly surfaced is generally called "collar". The lower part, which is the main body of the implant, is buried in the bone and support the whole implant against various stress generated in the oral cavity so that the implant may not be unsteady nor come out. The collar is smoothly surfaced so as to prevent various germs in the oral cavity from entering inward. But the collar, unlike the main body, does not contribute to fixation of the implant in the bone.

An implant is buried in the bone according to either non-submerged implant procedure or the submerged implant procedure. According to non-submerged implant procedure, the upper end of the buried implant projects through gingiva and is exposed in the oral cavity. As a result, a super structure can be mounted over the upper end of the implant without incising gingiva. According to the submerged implant procedure, however, the implant is completely buried in the bone. Thus, in order to mount the super structure over the upper end of the implant, several months after implantation, gingiva should be incised. The collar of the implant buried according to non-submerged implant procedure is from 5 to 10 mm long, while the collar of the implant buried according to the sub-merged implant procedure is shorter; about 0.5 to 2 mm.

The main body is supported in the bone generally with the help of mechanical anchoring of screw treads and/or rough surfaces. Recently, in addition, the surfaces of the main body of the implant are sometimes coated with biologically active material(s) so that the implant is chemically bonded to the bone and more stably supported.

Materials used for the implants may be selected from: metals such as titanium, titanium alloy, stainless steel, and so on; and ceramics such as alumina, zirconia, and so on.

The biologically active materials described above may be selected from biologically active glass, biologically active glass ceramics, hydroxyapatite, and so on. The surfaces of the main body are coated with said biologically active material(s) by binding with an adhesive, the fusion method, the thermal spray method, ion plating, and so on. Otherwise, the main body itself is made of such biologically active material(s).

A cylinder-type endosseous implant may have screw threads around the main body. In this case, the diameter of the collar serving as the head of the screw is designed to be greater than that of the screw threads.

The cylinder-type implant having screw threads can be buried according to one of two methods: the non-self-tapping implantation method (hereinafter referred to as implantation method A) and self-tapping implantation method (hereinafter referred as implantation method B). According to the implantation method A, a threaded hole (perforated site) is tapped and the implant is thread-fastened with the threaded hole. According to the implantation method B, a cylindrical or conical hole is drilled in the jaw bone and the implant which is provided with a self-tapping mechanism (such as cutting blades) screws into the perforated site.

An implant whose main body is roughly surfaced and, at the same time, can be buried according to the self-tapping implantation method B has not yet been put into practical use.

SUMMARY OF THE INVENTION

If the surfaces of the implant come in contact with the bone immediately after implantation with no gap in between, and if the implant is steadily supported, the implant is rapidly and stably bonded to the bone and will not easily come out. As the implants provided with the self-tapping mechanism can be supported in such a desirable condition, they do not easily come out. Accordingly, it is preferable to employ, if possible, the self-tapping implantation method B instead of method A which has been mainly employed.

The implantation method A, however, has a disadvantage. According to this method, the implant can not be buried or can not be smoothly buried in a hard bone.

When an implant having screw threads is roughly surfaced to increase affinity with the bone, the implantation method A can not be employed because of too much resistance during implantation operation against the rough surface having large surface area. As a result, the roughly surfaced implants having screw threads have been usually buried according to the implantation method A at the cost of good bearing capacity in the bone.

The object of the present invention is to provide an endosseous implant which is roughly surfaced and, at the same time, can be buried even in the hard bone according to the self-tapping implantation method, thereby realizing both good bearing capacity in the bone and high affinity with the bone.

In order to achieve this object, the first embodiment of the endosseous implant according to the present invention is a cylinder-type endosseous implant consisting of a collar portion and a main body portion formed under the collar portion, wherein screw threads having a height of 0.2 to 0.4 mm and a pitch of 0.8 to 1.7 mm are formed around said main body portion. More specifically, in the cross-section along the rotation axis of the implant, the straight line which could be drawn from the top of a screw thread (from the lower edge, or the edge near the lower end of the implant, of the ridge, if the screw thread has one, of the screw thread) to the bottom of the same screw thread is designed at an angle $\theta$, at least 50° and smaller than 90°, to the root surface (hereinafter the angle $\theta$ is referred as rising angle $\theta$ of the screw threads).

The second embodiment of the endosseous implant according to the present invention is a cylinder-type endosseous implant consisting of a collar portion and a main body portion provided with screw threads having a height of 0.2 to 0.4 mm and a pitch of 0.8 to 1.7 mm, wherein the rising angle $\theta$ of the screw thread is designed to be from 60° to 75°.

The third embodiment of the endosseous implant according to the present invention is a cylinder-type endosseous implant consisting of a collar portion and a main body portion provided with screw threads, wherein the lower end of the main body portion is cut to form one or more cutting surfaces as well as one or more clearance surfaces, and the entire main body portion including said cutting surface(s) and said clearance surface(s) is roughly surfaced.

The fourth embodiment of the endosseous implant according to the present invention is a cylinder-type endosseous implant consisting of a collar portion and a main body portion provided with screw threads, wherein the lower end of the main body portion is cut to form one or more cutting surfaces smoothly finished as well as one or more clearance surfaces also smoothly finished, and the rest of the main body portion is roughly surfaced.

Figures 3A, 3B, 4:
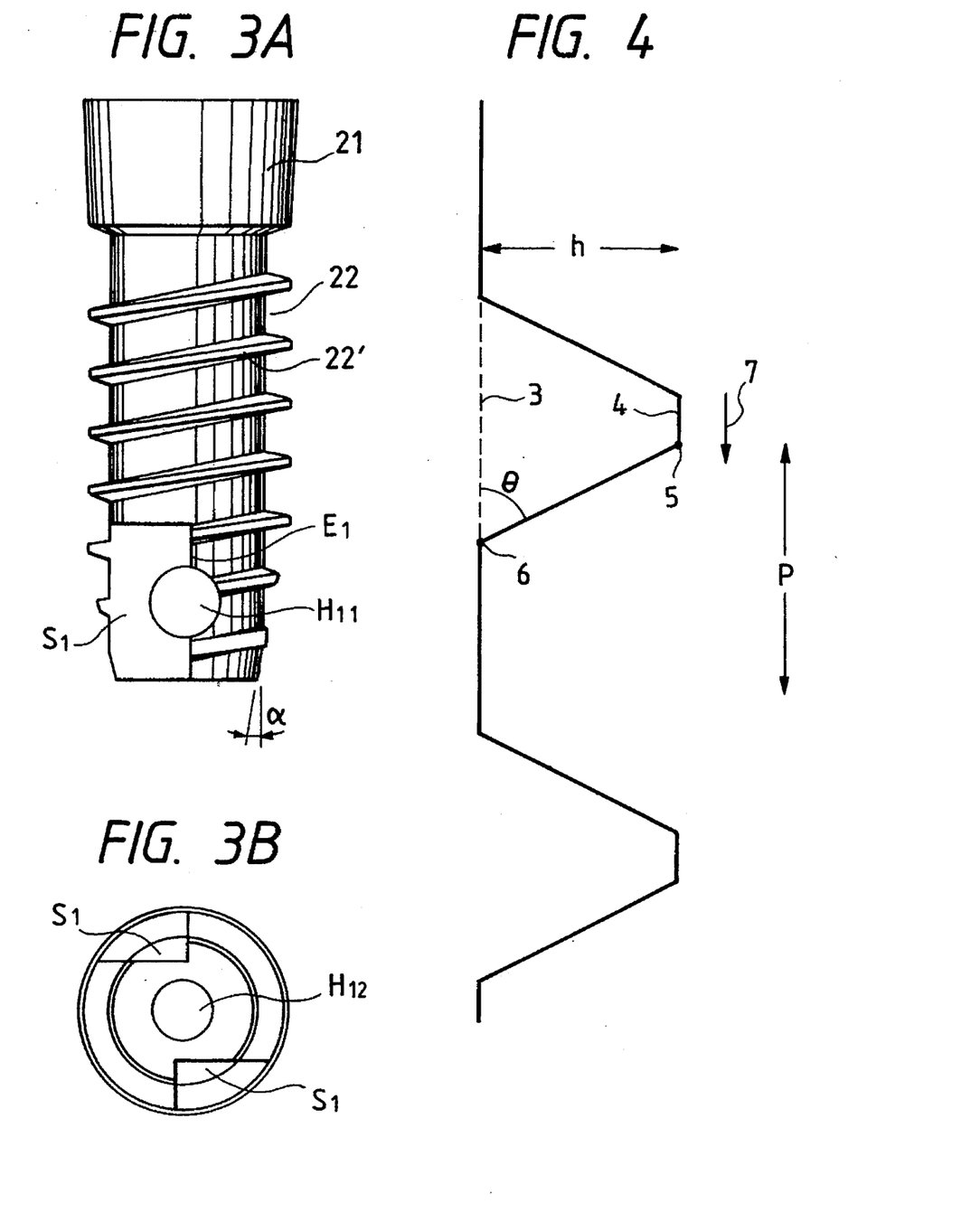
FIG. 3A is a side view of a third preferred embodiment of the endosseous implant according to the present invention.
FIG. 3B is a bottom view of the same.
FIG. 4 is a schematic view to illustrate parameters of the screw thread formed in the main body of an implant.

The present invention is based on the finding obtained with a great effort of the inventors that the height h of the screw threads, the pitch P of the same and the rising angle $\theta$ of the same (the angle at which the straight line from the lower edge 5 of the ridge 4 of a screw thread to the bottom 3 of the same screw thread is designed with respect to the base (root) 3 of the screw thread, see FIG. 4) are important parameters in improving initial fixation of the self-tapping implant and realising a rapid and stable bond of the implant and the bone after implantation. Note that the above expression "the lower edge 5" means the edge of the ridge near the lower end of the main body to the direction of which the implant is screwed (see FIG. 4).

If the height h of the screw threads is too great, the implant can not be buried in the narrow bone nor smoothly buried in the bone because of great resistance during implantation. On the other hand, if the height h of the screw thread is too small, initial fixation of the implant is not sufficient because of weak engagement of the screw threads. In this case, the implant is not stably supported by such weak engagement and sometimes forcedly screwed after the completion of implantation to run idly. On account of said reason, the height h of the screw thread is determined to be from 0.2 mm to 0.4 mm according to the present invention.

If the pitch P of the screw threads is too wide, the advance per screw (the lead) of the implant becomes too big. In this case, the implant can not be smoothly buried because resistance during implantation is too great and the implant can not be steadily screwed. On the other hand, if the pitch P of the screw thread is too narrow, it takes a long time to complete implantation and the inner surface of the bone which is carved with the screw threads easily crumbles. In consideration of said reason, the pitch P of the screw threads is determined to be from 0.8 to 1.7 mm.

On the basis of experiments on implantation, the rising angle $\theta$ of the screw threads is preferably determined to be at least 50° and less than 90°, and most preferably in a range from 60° to 75°.

Though the shape of the cross-section of the screw threads can be freely designed, the screw threads having smaller cross sections do not have to scrape a lot from the bone during implantation. The bone can be cut easily when the shape of a thread is a triangle cross section other than a trapezoidal, rectangular or sawtooth-like cross section. As both tensile stress and compressive stress are given to the implant during mastication, the shape of the cross section of the screw threads is preferably well-balanced and symmetrical with respect to stress from both directions in order to mitigate the load given to the implant.

The outline of the cross section of the screw threads does not have to consist of only strait lines, but part of or the entire outline may be designed as curved line(s). The top of a screw thread need not be pointed, but may have a ridge of some width. On account of facility of machining, the shape of the top of a screw thread is in practice, often designed to have a flat ridge or a ridge having certain curvature.

The maximum roughness $R_{max}$ (JISB601) of the surfaces of the main body should be preferably between 10 and 100 μm and, in particular, $R_{max}$ between 20 and 50 μm contributes to improvement over bone affinity, to obtaining stable initial fixation of implantation as well as rapid establishment of the steady bond between the implant and the bone after implantation. More specifically, if the roughness of the surfaces is not sufficient, good initial fixation, that is, reliable mechanical anchoring between the implant and the bone, can not obtained. On the other hand, the main body having very rough surfaces may, if exposed in the oral cavity, allow germs to propagate and cause infection, which often leads to bone resorption. Accordingly, the roughness of the main body surfaces of the implant should be controlled so as not to exceed a certain degree, whose $R_{max}$ (JISB601) is preferably in a range from 20 to 50 µm.

Materials preferably used for the collar portion and the main body of the implant according to the present invention may be selected from titanium, titanium alloys, transition metals such as cobalt, chromium and others, biologically non-active ceramics such as alumina, zirconium oxide and others, and biologically active materials (including certain ceramics, glass, glass ceramics, and so on). Examples of glass ceramics are ABC and AW.

When the main body is made of a metal or biologically non-active ceramics, it is preferably coated with a biologically active material to form a biologically active layer. The bone conduction effect of the biologically active material enhances early development of the bond between the implant and the bone. That is, the biologically active material layer of the main body portion of the implant can help the material of the main body to be easily caught by and engaged with the bone to establish steady bond to the bone faster than the surfaces of the main body without such a biologically active layer.

In order to provide a biologically active layer on the surfaces of the main body of the implant, certain preliminary treatment is carried out. For example, the surfaces of the main body is cleansed and finished roughly by abrasive blasting. Preferably, thus treated surfaces are further subjected to chemical treatment such as etching with an acid or anodic oxidation in order to increase the surface specific area. For surfaces having larger contact area with the biologically active material can have a strong layer thereof.

Preferably, the biologically active layer is formed as thinly as possible on the surfaces of the main body. Otherwise, the surfaces of the main body may be preferably spotted with the biologically active material so that larger part of the surfaces are exposed to the bones without the biologically active layers. Thus spotted biologically active layers do not hinder direct contact of the main body and the bone, and the exposed part of the main body can be easily caught by and engaged with the bone.

Preferable biologically active materials used to form the biologically active layer may be selected from, for example, hydroxy apatite, calcium triphosphate, biologically active glass or glass ceramics (see, for example, J. Biomed. Mater. Res. Symp. No. 2 (Part 1) pp. 111–141 (1971), Japanese Patent Application Laid-open Nos. 50-21015, 51-106114, 53-145394, 54-17, 54-135496, 57-3739, 58-118746, and others), sintered bodies of apatite disclosed in Japanese Patent Application Laid-open No. 62-052163, and so on.

The biologically active layer is preferably formed according to, for example, a gas phase technique such as vapor deposition, CVD, sputtering, ion plating, and so on, a solid phase technique such as thermal spray method, sintering process, and so on, or a liquid phase technique such as anodic oxidation, and so on.

In order to increase adhesion of the biologically active layer to the surfaces of the main body of the implant, an intermediate layer may be provided between the surfaces of the main body and the biologically active layer. The intermediate layer may be composed with a gradient of components. In this case the inner side of the intermediate layer facing on the surfaces of the main body contains mainly or only a material specific to the intermediate layer, while the outer side of the intermediate layer facing on the biologically active layer contains mainly or only the same biologically active material of which the biologically active layer is made.

Figure 2A:
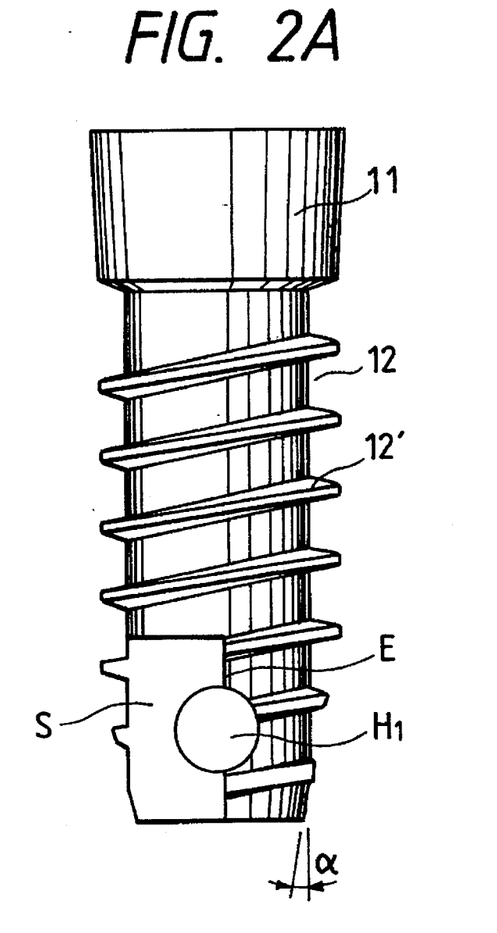
FIG. 2A is a side view of a second preferred embodiment of the endosseous implant according to the present invention.
Figure 2B:
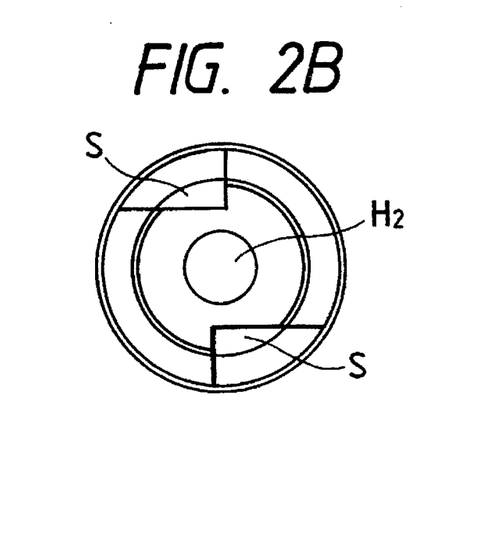
FIG. 2B is a bottom view of the same.
Figure 5A:
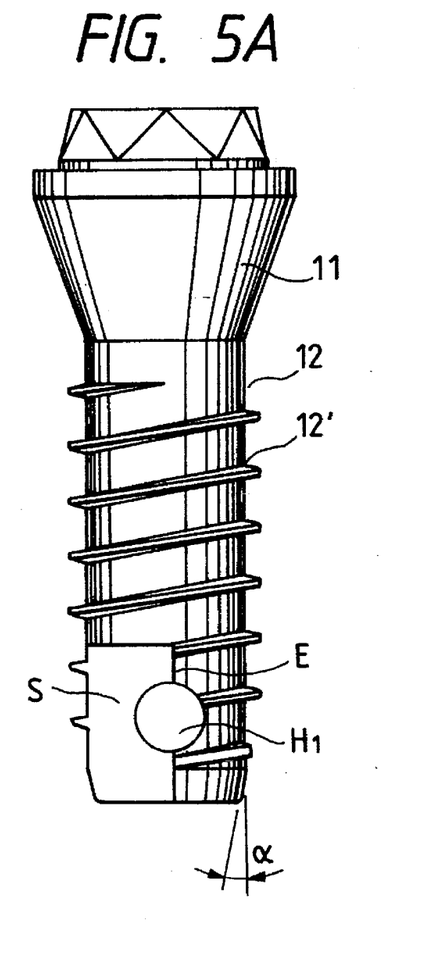
FIG. 5A is a side view of a fourth preferred embodiment of the endosseous implant according to the present invention.
Figure 5B:
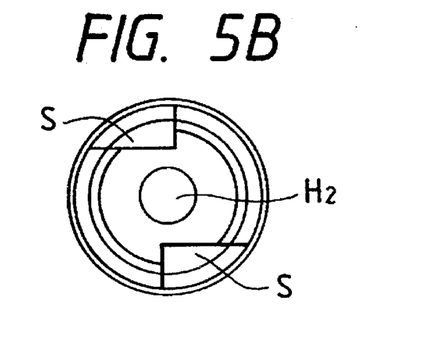
FIG. 5B is a bottom view of the same.

An endosseous implant according to the present invention shown in FIGS. 2A, 2B, 5A and 5B has a main body 12 which is provided with male threads 12' and has its end cut to have one or more niches S each consisting of a cutting surface and a clearance surface (The implant shown in FIGS. 2B and 5B exemplifies a main body having two niches S). The entire main body 12 including the male thread 12' and the niche(s) S, is roughly surfaced.

Another endosseous implant according to the present invention shown in FIGS. 3A, 3B, 6A and 6B has a main body 22 which is also provided with male threads 22' and has its end cut to have one or more niches S1. The main body 22, however, is not entirely roughly surfaced. That is, the cutting surface and the clearance surface of each niche S1 are smoothly surfaced.

These two types of endosseous implants can be buried in the bone according to the self-tapping implantation method, which has been demonstrated by experiment carried out both in vitro and in vivo. If preferably, the collar portions 11 and 21 can be omitted.

A preferable example of the shape of the male treads 12' and 22' has a height h of 0.2 to 0.4 mm, a pitch P of 0.8 to 1.7 mm and a rising angle θ of, at least, 50° and less than 90° (more preferably in a range from 60° to 75°) (see FIG. 4). The shape of the male treads 12' and 22', however, is not limited to this example.

The roughness of the surfaces of the main bodies 12 and 22 preferably does not exceed a certain degree, which is preferably in a range from 10 to 100 µm, more preferably from 20 to 50 µm in order to improve affinity with the bone as well as reduce resistance during self tapping implantation. Each niche S1 has its cutting surface and its clearance surface smoothly finished so the endosseous implant shown in FIGS. 3A, 3B, 6A and 6B can be easily buried according to the self-tapping implantation method. But, the endosseous implant shown in FIGS. 2A, 2B, 5A and 5B which has roughly surfaced niche(s) S also exhibits a sufficient self tapping function.

It is preferable to form one or more through holes (indicated as H1 in FIG. 5A and as H11 in FIG. 6A), wherein the brims of each through hole (H1, H11), or at least part of the brims, overlap with their respective niches (S, S1) formed on the surface of the end portion of the main body (12, 22). As the implants according to the present invention are provided with said through holes (H1, H11) the bone chips scraped during self-tapping implantation do not stay between the bone and the implants, but are received into the through holes (H1, H11), which prevents bone resorption from the main body surface. In addition, as new bone is produced in the through holes H1 and H11, the functions of the implants are improved.

In favor of functions of the implants as well as the manufacture thereof, the through holes H1 and H11 are drilled vertical to the rotation axes of the implants.

Preferably tip holes H2 and H12 (see FIGS. 2B, 3B, 5B and 6B) which communicate with the through holes H1 and H11, respectively are provided as the tips of the implants. Note that these tip holes H2 and H12 do not communicate with the screw hole which locate on the top surface of the implant. By forming the tip holes H2 and H12, the bone chips scraped during implantation are easily led through the tip holes H2 and H12 into the through holes H1 and H11. Thus, new bone can be produced not only in the through holes H1 and H11 but also in the tip holes H2 and H12.

The tip faces (the lower ends) of the implants are surfaced either roughly or smoothly. And in favor of functions of the implant as well as the manufacture thereof, the tip holes H2 and H12 are preferably formed in parallel with the rotation axes of the implants.

The through holes H1 and H11 and/or the tip holes H2 and H12 are preferably circular in favor of functions of the implants and faciling of manufacture. Especially circular tip holes H2 and H12 are desirable.

It is further preferable to the function of the implants and manufacture thereof to provide only one tip hole at each tip end and, at the same time, form it coaxially with the implant.

It is preferable to reproduction of the bone to roughly surface the inner surfaces of the through holes H1 and H11 as well as those of the tip holes H2 and H12. But even when the inner surfaces are not rough, the scraped bone chips can be effectively received in the holes.

Further, it is preferable to form an even number of said niches S (or S1) to each implant and, at the same time, arranged the niches S (or S1) rotation-symmetrically with respect to the rotation axis of the implant because the implant can be reliably and easily buried according to the self tapping implantation method and the implant itself is easy to manufacture. Said even number is most preferably 2, 4 or 8.

In preferable construction, the brims of a circular through hole H1 (H11) overlap their respective niches S (S1) so that the center of the through hole H1 (H11) may coincide with the edge E (E1) of the niches S (S1), that is, the axis of the through hole H1 (H11) max exist in a plane including the cutting surfaces of the niches S (S1). According to this construction, the scraped bone chips are effectively led into the through hole H1 (H11) and the implant can be reliably and easily buried according to the self-tapping implantation method. In addition, the implant having said construction is easy to manufacture.

The edge of the end face of the implant is preferably tapered at an angle α, which is in a range from 5° to 15°. Thus tapered implant, which has circular-truncated-conical tip, can be easily screwed in the perforated site.

If the angle α is not more than 5°, it is not very easy to insert the implant into the perforated site. On the other hand, if the angle α is more than 15°, the tip of the implant becomes too slender. In this case, excessive stress may concentrate in the slender tip portion during mastication, which is problemsome.

As described above in detail, endosseous implants according to the present invention which have roughly surfaced main bodies and are easy to bury according to the self tapping implantation method can be stably supported in the bone and exhibit excellent affinity with the bone.

When the bone is very hard, it is preferable to tap part of the inner surface, near the brim, of the perforated site, that is, to employ the non-self-tapping implantation method in combination with the self-tapping implantation method so that the self-tapping implantation in the deeper portion of the perforated site may be easily executed. In this case, the roughly surfaced main body can come into sufficient contact even with the tapped portion of the bone.

DESCRIPTION OF THE PREFERRED EMBODIMENTS

The present invention will be described below in detail with reference to its preferable embodiments. The present invention, however, is not limited to the following embodiments.

Embodiment 1

Figure 1:
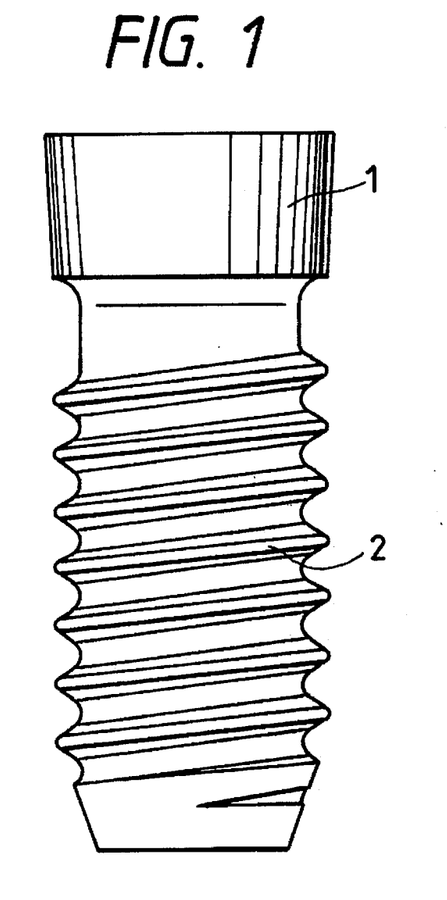
FIG. 1 is a schematic side view of a first preferred embodiment of the endosseous implant according to the present invention.

Plurality of cylinder-type implants (the root diameter; 2.7 mm, the overall length; 10 mm, and the length of the collar portion 1; 2 mm) for the two-step implantation method were prepared so as to have various types of screw threads around the main bodies 2 (see FIG. 1). The screw threads are different in certain parameters: the height h of the screw threads; the pitch P of the same, and the angle θ, made by the root surface and the straight line which could be drawn from the top of a screw thread (from the lower edge, or the edge near the lower end of the implant, of the ridge, if the screw thread has one, of the screw thread) to the bottom of the same screw thread (see FIG. 4). The implants having different types of screw threads are listed in Table 1. Note that, hereinafter, the angle θ described above will be referred to as the rising angle θ of the screw thread.

Experiments were carried out in which each implant was buried in the perforated site in the pig jaw bone without tapping the perforated site and implantation of the implant was examined. Table 2 shows the result of the experiments. The jaw bone was first drilled to form a parallel perforated site having a diameter of 2.7 mm, which is the same as the root diameter of the screw threads. And then, the brim of the perforated site was enlarged by a tapered drill (countersink) to fit with the shape of the collar portion.

The implantation of each implant was examined from four aspects:

initial bite, or how easily the screw threads can bite into the bone at the early stage of implantation;

advance, or how rectilinearly the implant can be screwed into the bone with little deviation;

smoothness or how smoothly the bone can be cut with little resistance against the implant during implantation; and distinct completion, or how sharply resistance against the implant increases when the collar portion of the implant comes into contact with the enlarged brim of the perforated site and the implantation is completed. General estimation of the implantation of each implant was obtained on the basis of the above four aspects.

The most considerable demerit of an implant having screw threads is indistinct completion of implantation operation. As the completion is hard to judge, the implant may often be screwed in too deeply to break the bone. In this case, the implant idly runs in the broken perforated site after implantation. On the other hand, when the implant is not sufficiently screwed in the perforated site for fear of breaking the bone, excellent initial fixation can not be obtained and the implant sometimes comes out. Accordingly, distinct completion is the most heavily weighed factor of the four aspects of estimation of the implantation.

According to such estimation, implants Nos. 4, 5, 7, 8, 13, 14, 16, 17 were judged to be applicable for practical use. All of these practically applicable implants satisfied the following conditions: the height h of the screw threads is 0.2 to 0.4 mm; the pitch P of the screw thread is 0.8 to 1.7 mm and the rising angle θ of the screw threads is at least 50° and less than 90°.

Well performing implants Nos. 4, 7 and 14 selected from the above-mentioned practically applicable implants as well as unsatisfactory implants Nos. 9, 18 and 26 were subjected to plasma spray to coat the main bodies with titanium and surface them with roughness not exceeding a certain degree, whose $R_{max}$ was in a range from 20 to 50 μm. Estimation of the implantation of each roughly surfaced implant was carried out in the same way. The implants Nos. 4, 7 and 14, which were already deemed good performers were found to be further improved after coating with titanium, while the unsatisfactory implants Nos. 9, 18 and 26 exhibited little improvement.

TABLE 1

Implants Subjected to Estimation

| Implant No. | h (mm) | θ (deg) | P (mm) |
| --- | --- | --- | --- |
| 1 | 0.15 | 75 | 1.00 |
| 2 | 0.15 | 75 | 1.50 |
| 3 | 0.15 | 75 | 2.00 |
| 4 | 0.25 | 75 | 1.00 |
| 5 | 0.25 | 75 | 1.50 |
| 6 | 0.25 | 75 | 2.00 |
| 7 | 0.35 | 75 | 1.00 |
| 8 | 0.35 | 75 | 1.50 |
| 9 | 0.35 | 75 | 2.00 |
| 10 | 0.15 | 60 | 1.00 |
| 11 | 0.15 | 60 | 1.50 |
| 12 | 0.15 | 60 | 2.00 |
| 13 | 0.25 | 60 | 1.00 |
| 14 | 0.25 | 60 | 1.50 |
| 15 | 0.25 | 60 | 2.00 |
| 16 | 0.35 | 60 | 1.00 |
| 17 | 0.35 | 60 | 1.50 |
| 18 | 0.35 | 60 | 2.00 |
| 19 | 0.15 | 45 | 1.00 |
| 20 | 0.15 | 45 | 1.50 |
| 21 | 0.15 | 45 | 2.00 |
| 22 | 0.25 | 45 | 1.00 |
| 23 | 0.25 | 45 | 1.50 |
| 24 | 0.25 | 45 | 2.00 |
| 25 | 0.35 | 45 | 1.00 |
| 26 | 0.35 | 45 | 1.50 |
| 27 | 0.35 | 45 | 2.00 |
| 28 | 0.15 | 90 | 1.50 |
| 29 | 0.25 | 90 | 1.50 |
| 30 | 0.35 | 90 | 1.50 |

TABLE 2

Result of Estimation of Implantation
(○; good, △; medium, X; bad)

| Implant No. | Initial Bite | Advance | Smoothness | Distinct Completion | General Estimation |
| --- | --- | --- | --- | --- | --- |
| 1 | △ | ○ | ○ | X | X |
| 2 | △ | ○ | ○ | X | X |
| 3 | △ | ○ | ○ | X | X |
| 4 | △ | ○ | ○ | △ | △ |
| 5 | △ | ○ | ○ | △ | △ |
| 6 | △ | X | △ | △ | X |
| 7 | X | ○ | ○ | ○ | ○ |
| 8 | X | ○ | ○ | ○ | ○ |
| 9 | X | X | X | ○ | X |
| 10 | △ | ○ | ○ | X | X |
| 11 | △ | ○ | ○ | X | X |
| 12 | △ | ○ | ○ | X | X |
| 13 | △ | ○ | ○ | △ | △ |
| 14 | △ | ○ | ○ | △ | △ |
| 15 | △ | X | △ | △ | X |
| 16 | X | ○ | ○ | ○ | ○ |
| 17 | X | ○ | △ | ○ | △ |
| 18 | X | X | X | ○ | X |
| 19 | △ | ○ | ○ | X | X |
| 20 | △ | ○ | ○ | X | X |
| 21 | △ | ○ | ○ | X | X |
| 22 | X | ○ | △ | △ | X |
| 23 | X | ○ | X | △ | X |
| 24 | X | ○ | X | △ | X |
| 25 | X | ○ | X | ○ | X |
| 26 | X | ○ | X | ○ | X |
| 27 | X | X | X | ○ | X |
| 28 | △ | △ | ○ | X | X |
| 29 | X | △ | ○ | △ | X |
| 30 | X | △ | ○ | ○ | X |

Embodiment 2

Plurality of cylinder-type implants (the overall length; 10 mm, and the length of the collar portion 11; 2 mm) for the two-step implantation method was prepared, wherein the main body 12 of each implant was provided with male threads 12' (the root diameter; 2.7 mm, the height h of the screw threads; 0.25 mm, the pitch P of the screw threads; 1 mm, the rising angle θ of the screw thread; 75°, and the taper angle α of the tip of the main body 12; 10°). (see FIGS. 2A and 2B). The entire surfaces of the main body 12, including the male threads 12' and niche(s) S each consisting of a cutting surface and a clearance surface were roughly surfaced to have roughness not exceeding a certain degree, whose $R_{max}$ was in a range from 20 to 50 μm. The resultant implants will be referred to as implants A.

Similarly, implants B were prepared, which were the same as said implants A except the following parts of construction. Specifically two niches S were formed in the tip portion of the main body 12 having the male threads 12' so that niches S were arranged rotation-symmetrically with respect to the rotation axis of the implant B. And a cylindrical through hole H1 having a diameter of 1.2 mm was formed so that the centers of the openings of the through hole H1 might coincide with their respective edges E of the clearance surfaces of the niches S. Further, in the tip end face of the implant B, a cylindrical tip hole H2 having a diameter of 1.0 mm and communicating with said through hole H1 was formed coaxially with the implant B. Accordingly, the through hole H1 and the tip hole H2 communicated with each other and were arranged vertically to each other inside the main body 12 of the implant B.

Implants C were different from the implants B in that the taper angle α was 2° while that of the implants B was 10°. And implants D were similarly prepared, which differed from the implants B in that the $R_{max}$ of the surfaces was controlled not to exceed 120 μm.

Experiments were carried out, in which implants A to D were buried in the pig jaw bones according to the self tapping implantation method. The conditions of implantation of each implant were qualitatively examined. Table 3 shows the result of the experiments. As in the experiments of Embodiment 1, the jaw bones were first drilled to form parallel perforated sites having the same diameter as the root diameter of the male threads 12'. And then, the brims of the perforated sites which would come into contact with the collar portions 11 of the implants were enlarged by a tapered drill (countersink) to fit with the collar portions 11.

The implantation of each implant was examined from the above-mentioned four aspects: initial bite, advance, smoothness and distinct completion.

According to general estimation, the implants B, which were the most highly rated, were found to exhibit better initial bite as well as more smoothness than the implants A. The implants C having the smaller taper angle α could not exhibit as an initial bite as the implants B. The implants D whose surfaces had $R_{max}$ exceeding 100 μm met great resistance during implantation.

TABLE 3

Result of Estimation of Implantation
(⊚; excellent, O; good, Δ; medium, X; bad)

| Implant | Initial Bite | Advance | Smoothness | Distinct Completion | General Estimation |
|---------|--------------|---------|------------|---------------------|--------------------|
| A | Δ | O | O | Δ | Δ |
| B | O | O | ⊚ | Δ | O |
| C | Δ | O | ⊚ | Δ | Δ |
| D | O | O | Δ | Δ | Δ |

Embodiment 3

Plurality of cylinder-type implants (the overall length; 10 mm, and the length of the collar portion 21; 2 mm) for the two-step implantation method were prepared, wherein the main body 22 of each implant was provided with male threads 22' (the root diameter; 2.7 mm, the height h of the screw threads; 0.25 mm, the pitch P of the screw threads; 1.0 mm, the rising angle θ of the screw threads; 75°, and the taper angle α of the tip of the main body 22; 10°). (see FIGS. 3A and 3B). The main bodies 22 including the male threads 22' were roughly surfaced so as to have roughness not exceeding a certain degree, whose $R_{max}$ was in a range from 20 to 50 μm.

Next, two niches S1 each consisting of a cutting surface and a clearance surface were formed in the tip portion of the main body 22 having the male threads 22' so that niches S1 are arranged rotation-symmetrically with respect to the rotation axis of the implant. Note that the cutting surfaces and the clearance surfaces of the niches were not roughly surfaced. Then, a cylindrical through hole H11 having a diameter of 1.2 mm was formed so that the centers of the openings of the through hole H11 might coincide with their respective edges E1 of the clearance surfaces of the niches S1. Further, in the tip end face of the implant, a cylindrical tip hole H12 having a diameter of 1.0 mm and communicating with said through hole H11 was formed coaxially with the implant. Accordingly, the through hole H11 and the tip hole H12 communicated with each other and were arranged vertically to each other inside the main body 22 of thus prepared implant, which will be referred as the implant F.

Implants G, which were different from the implants F only in that the cutting surfaces and the clearance surfaces of the niches S1 were roughly surfaced, were similarly prepared.

Experiments were carried out, in which implants F and G were buried in the pig jaw bones according to the self tapping implantation method. The conditions of implantation of each implant were qualitatively examined. Table 4 shows the result of the experiments. As in the experiments of Embodiments 1 and 2, the jaw bones were first drilled to form parallel perforated sites having the same diameter as the root diameter of the male threads 22'. And then, the brims of the perforated sites which would come into contact with the collar portions 21 of the implants were enlarged by a tapered drill (counter-sink) to fit with the collar portions 21.

The implantation of each implant was examined from the above-mentioned four aspects: initial bite, advance, smoothness and distinct completion.

According to general estimation, the implants F having smoothly surfaced niches S1 exhibited advanced and distinct completion similar to those of the implants G having roughly surfaced niches S1. The implants F, however, exhibited better initial bite and more smoothness than the implants G. Thus, the implants F were generally better than the implants G.

TABLE 4

Result of Estimation of Implantation
(⊚; excellent, O; good, Δ; medium, X; bad)

| Implant | Initial Bite | Advance | Smoothness | Distinct Completion | General Estimation |
|---------|--------------|---------|------------|---------------------|--------------------|
| F | ⊚ | O | ⊚ | Δ | ⊚ |
| G | O | O | ⊚ | Δ | O |

Embodiment 4

Plurality of cylinder-type implants (the overall length; 10 mm, and the length of the collar portion 11; 2 mm) for the single-step implantation method were prepared, wherein the main body 12 of each implant was provided with male threads 12' (the root diameter; 2.7 mm, the height h of the screw threads; 0.25 mm, the pitch P of the screw threads; 1.0 mm; the rising angle θ of the screw threads; 75°, and the taper angle α of the tip of the main body 12; 10°) (see FIGS. 5A and 5B). The entire surfaces of the main body 12, including the male threads 12' and niche(s) S each consisting of a cutting surface and a clearance surface and formed in the tip portion of the main body 12, were roughly surfaced so as to have roughness not exceeding a certain degree, whose $R_{max}$ was in a range from 20 to 50 μm. Thus prepared implants will be referred as the implants I.

Similarly, implants J were prepared, which were the same as said implants I except the following parts of construction. Specifically two niches S were formed in the tip portion of the main body 12 having the male threads 12' so that niches S were arranged rotation-symmetrically with respect to the rotation axis of the implant J. And a cylindrical through hole H1 having a diameter of 1.2 mm was formed so that the centers of the openings of the through hole H1 might coincide with their respective edges E of the clearance surfaces of the niches S. Further, in the tip end face of the implant J, a cylindrical tip hole H2 having a diameter of 1.0 mm and communicating with said through hole H1 was formed coaxially with the implant J. Accordingly, the through hole HI and the tip hole H2 communicated with each other and were arranged virtically to each other inside the main body 12 of the implant J.

Implants K were similarly prepared, which were different from the implants J in that the taper angle α was 2° while that of the implant J was 10°. And implants L were also prepared, which differed from the implants J in that $R_{max}$ of the surfaces was controlled not to exceed 120 μm.

Experiments were carried out, in which implants I to L were buried in the pig jaw bones according to the self-tapping implantation method. The conditions of implantation of each implant were qualitatively examined. Table 5 shows the result of the experiments. As in the experiments of the above-mentioned Embodiments 1, 2 and 3, the jaw bones were first drilled to form parallel perforated sites having the same diameter as the root diameter of the male threads 12'. And then, the brims of the perforated sites which would come into contact with the collar portions 11 of the implants were enlarged by the countersink so as to fit with the collar portions 11.

The implantation of each implant was examined from the above-mentioned four aspects, that is, initial bite, advance, smoothness and distinct completion.

According to general estimation, the implants J, which were the most highly rated, were found to exhibit better initial bite as well as more smoothness than the implants I. The implants K having the smaller taper angle α could not exhibit as good initial bite as the implants J. The implants L whose surfaces had roughness exceeding 100 μm met great resistance during implantation.

TABLE 5

Result of Estimation of Implantation
(⊚; excellent, O; good, Δ; medium, X; bad)

| Implant | Initial Bite | Advance | Smoothness | Distinct Completion | General Estimation |
| --- | --- | --- | --- | --- | --- |
| I | Δ | O | O | Δ | Δ |
| J | O | O | ⊚ | Δ | O |
| K | Δ | O | ⊚ | Δ | Δ |
| L | O | O | Δ | Δ | Δ |

Embodiment 5

Figure 6A:
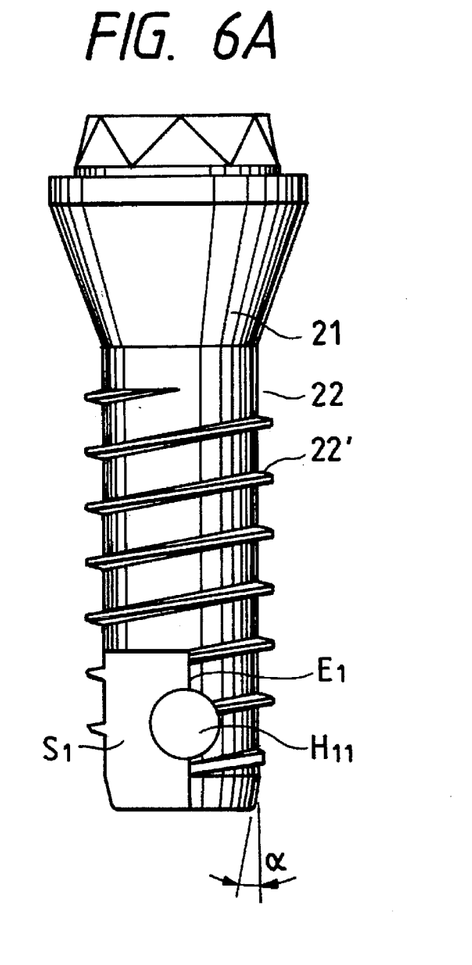
FIG. 6A is a side view of a fifth preferred embodiment of the endosseous implant according to the present invention.
Figure 6B:
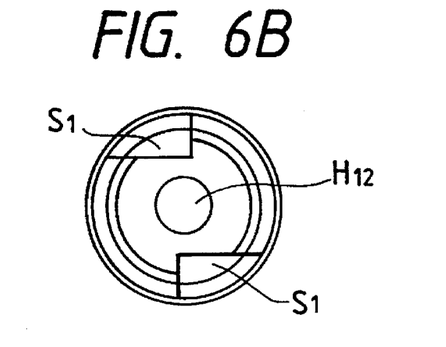
FIG. 6B is a bottom view of the same.

Plurality of cylinder-type implants (the overall length; 10 mm, and the length of the collar portion 21; 2 mm) for the single-step implantation method were prepared, wherein the main body 22 of each implant was provided with male threads 22' (the root diameter; 2.7 mm, the height h of the screw threads; 0.25 mm, the pitch P of the screw threads; 1.0 mm, the rising angle θ of the screw threads; 75°, and the taper angle α of the tip of the main body 22; 10°) (see FIGS. 6A and 6B). The main bodies 22 including the male threads 22' were roughly surfaced so as to have roughness not exceeding a certain degree, whose $R_{max}$ was in a range from 20 to 50 μm.

Next, two niches S1 each consisting a cutting surface and a clearance surface were formed in the tip portion of the main body 22 of each implant having the male threads 22' so that the niches S were arranged rotation-symmetrically with respect to the rotation axis of the implant. Note that the cutting surfaces and the clearance surfaces of these niches S were not roughly surfaced but were smooth. Then, a cylindrical through hole H11 having a diameter of 1.2 mm was formed so that the centers of the openings of the through hole H11 might coincide with their respective edges E1 of the clearance surfaces of the niches S1. Further, in the tip end face of the implant, a cylindrical tip hole H12 having a diameter of 1.0 mm and communicating with said through hole H11 was formed coaxially with the implant. Accordingly, the through hole H11 and the tip hole H12 communicated with each other and were arranged vertically to each other inside the main body 22 of the thus prepared implant, which will be referred as the implant M.

Implants N, which were different from the implants M only in that the cutting surfaces and the clearance surfaces of the niches S1 were roughly surfaced, were similarly prepared.

Experiments were carried out, in which implants M and N were buried in the pig jaw bones according to the self tapping implantation method. The conditions of implantation of each implant were qualitatively examined. Table 6 shows the result of the experiments. As in the experiments of Embodiments 1, 2, 3 and 4, the jaw bones were first drilled to form parallel perforated sites having the same diameter as the root diameter of the male threads 22'. And then, the brims of the perforated sites which would come into contact with the collar portions 21 of the implants were enlarged by the countersink to fit with the collar portions 21.

The implantation of each implant was examined, as described before, from the four aspects: initial bite, advance, smoothness and distinct completion.

According to general estimation, the implants M having smoothly surfaced niches S1 exhibited advance and distinct completion similar to those of the implants N having roughly surfaced niches S1. The implants F, however, exhibited better initial bite and more smoothness than the implants N. Thus, the implants M were generally better than the implants N.

TABLE 6

Result of Estimation of Implantation
(⊚; excellent, O; good, Δ; medium, X; bad)

| Implant | Initial Bite | Advance | Smoothness | Distinct Completion | General Estimation |
| --- | --- | --- | --- | --- | --- |
| M | ⊚ | O | ⊚ | Δ | ⊚ |
| N | O | O | ⊚ | Δ | O |

As described in detail, the endosseous implants according to the present invention can be smoothly and stably buried even in a hard bone according to the self tapping implantation method. Accordingly, the implants do not easily come out and can be used in vivo over a long period of time.

As the endosseous implant according to the present invention has its main body, or part of its main body, roughly surfaced and is designed to be easily buried according to the self tapping implantation method, it can be stably supported in the bone and exhibit good affinity with the bone. Such good affinity with the bone is obtained mainly by well-controlled roughness of the surfaces of the main body.

In addition, the implant according to the present invention, when provided with one or more niches in the tip end portion of the main body having screw threads, can be more easily and more reliably buried according to the self-tapping implantation method. As a result, successful implantation can be easily carried out by employing the implant according to the present invention.

What is claimed is:

1. A cylinder-type endosseous implant comprising a collar portion and a main body portion formed under said collar portion and having screw threads disposed about said main body, the screw threads having a height from 0.2 to 0.4 mm;

a pitch from 0.8 to 1.7 mm;

and a rising angle from 50° to less than 90°, wherein the rising angle is defined to be the angle made by the surface of said main body portion and a straight line which could be drawn from the top of one of said screw threads to the bottom of the same screw thread.

2. A cylinder-type endosseous implant according to claim 1, wherein said main body portion further comprises a rough surface having a roughness not exceeding 20 to 50 µm.

3. A cylinder-type endosseous implant comprising a collar portion and a main body portion formed under said collar portion and having screw threads disposed about said main body; the screw threads having a height from 0.2 to 0.4 mm;

a pitch from 0.8 to 1.7 mm;

and a rising angle from 60° to 75°, wherein the rising angle is defined to be the angle made by the surface of said main body portion and a straight line which could be drawn from the top of one of said screw threads to the bottom of the same screw thread.

4. A cylinder-type endosseous implant according to claim 3, wherein said main body portion further comprises a rough surface having a roughness not exceeding 20 to 50 µm.

5. An endosseous implant comprising:

a collar portion: and a main body portion formed under said collar portion, having male threads with a height from 0.2 to 0.4 mm and a pitch from 0.8 to 1.7 mm provided about said main body portion, a tip portion at the end of said main body portion, and a niche formed in the tip portion, the niche of said main body portion having a cutting surface and a clearance surface, and the surface of said main body portion including the male threads, the tip portion, and the niche having a roughness not exceeding 10 to 100 µm.

6. An endosseous implant according to claim 5, which is made of a material selected from the group consisting of titanium, a titanium alloy, an oxide thereof or a compound thereof.

7. An endosseous implant according to claim 5, wherein said main body portion is made of a biologically active material.

8. An endosseous implant according to claim 5, wherein said main body portion further comprising a through hole provided in the tip portion of said main body portion, said through hole having a brim overlapping said niche.

9. An endosseous implant according to claim 5, further comprising a through hole in the tip portion of said main body portion, a tip end face on the end of the tip portion of said main body portion, and a tip hole in the tip end face, wherein the through hole has a brim overlapping said niche and the tip hole communicates with the through hole.

10. An endosseous implant according to claim 5 having a plurality of said niche, wherein the plurality of niches are arranged rotation-symmetrically with respect to the rotation axis of the implant.

11. An endosseous implant according to claim 5, wherein the tip end portion of said main body portion is tapered at an angle of 5° to 15°.

12. An endosseous implant comprising:

a collar portion; and a main body portion formed under said collar portion, having male threads with a height from 0.2 to 0.4 mm and a pitch from 0.8 to 1.7 mm provided about said main body portion, a tip portion at the end of said main body portion, and a niche formed in the tip portion, the niche of said main body portion having a cutting surface and a clearance surface, and the surface of said main body portion including the male threads and the tip portion having a roughness not exceeding 10 to 100 µm.

13. An endosseous implant according to claim 12, which is made of a material selected from the group consisting of titanium, a titanium alloy, an oxide thereof or a compound thereof.

14. An endosseous implant according to claim 12, wherein said main body is made of a biologically active material.

15. An endosseous implant according to claim 12, wherein said main body portion further comprising a through hole provided in the tip portion of said main body portion, said through hole having a brim overlapping said niche.

16. An endosseous implant according to claim 12, further comprising a through hole in the tip portion of said main body portion, a tip end face on the end of the tip portion of said main body portion, and a tip hole in the tip end face, wherein the through hole has a brim overlapping said niche and the tip hole communicates with the through hole.

17. An endosseous implant according to claim 12 having a plurality of said niche, wherein the plurality of niches are arranged rotation-symmetrically with respect to the rotation axis of the implant.

18. An endosseous implant according to claim 12, wherein the tip end portion of said main body portion is tapered at an angle of 5° to 15°.

19. A cylinder-type endosseous implant comprising:

a collar portion; and a main body portion formed under said collar portion and having screw threads disposed about said main body, the screw threads having a height from 0.2 to 0.4 mm and a pitch from 0.8 to 1.7 mm.

* * * * *